(12) United States Patent
Huang

(10) Patent No.: US 7,588,898 B2
(45) Date of Patent: Sep. 15, 2009

(54) BIOMARKER FOR GESTATIONAL TROPHOBLASTIC DISEASE

(75) Inventor: Wilber Huang, Taipei (TW)

(73) Assignee: Abnova (Taiwan) Corporation, Neihu, Taipei (TW)

( * ) Notice: Subject to any disclaimer, the term of this patent is extended or adjusted under 35 U.S.C. 154(b) by 22 days.

(21) Appl. No.: 11/804,288

(22) Filed: May 17, 2007

(65) Prior Publication Data

US 2008/0138810 A1 Jun. 12, 2008

Related U.S. Application Data

(60) Provisional application No. 60/841,667, filed on Aug. 31, 2006.

(51) Int. Cl.
*G01N 33/53* (2006.01)
*G01N 33/566* (2006.01)

(52) U.S. Cl. ........................ 435/7.1; 435/7.21; 436/501; 436/518

(58) Field of Classification Search ........................ None
See application file for complete search history.

(56) References Cited

OTHER PUBLICATIONS

Simard et al. (Endocrine Reviews, vol. 26, No. 4., 2005, pp. 525-582).*
Yang et al. (Journal of Molecular Endocrinology, vol. 37, No. 3, pp. 533-540).*
Shih et al. (International Journal of Gynecological Pathology, VI.20, pp. 31-47, 2001).*
K. Boon, E.C. Osorio, S.F. Greenhut, et al.; "An Anatomy of Normal and Malignant Gene Expression;" Proc. Natl Acad Sci U.S.A., 2002; pp. 11287-11292.
D.A. Budwit-Novotny, K.S. McCarty, E.B. Cox, et al.; "Immunohistochemical Analyses of Estrogen Receptor in Entometrial Adenocarcinoma Using a Monoclonal Antibody;" Cancer Res., 1986; pp. 5419-5425.
Y-C Chen, G. Pohl, T-L Wang, et al.; "Apolipoprotein E is Required for Cell Proliferation and Survival in Ovarian Cancer;" Cancer Res., 2005; pp. 331-337.
A. Lal, A.E. Lash, S.F. Altschul, et al.; "A Public Database for Gene Expression in Human Cancers;" Cancer Res., 1999; pp. 5403-5407.
B.A. Lessey, A.J. Castelbaum, L. Wolf, et al.; "Use of Integrins to date the Endometrium;" Fertil. Steril., 2000; pp. 779-787.
I.M. Shih, M. Nesbit, M. Herlyn, et al.; "A New Mel-Cam (CD146)-Specific Monoclonal Antibody, MN-4, on Paraffin-Embedded Tissue;" Mod. Pathol., 1998; pp. 1098-1106.
K. Nakayama, N. Nakayama, B. Davidson, et al.; "A BTB/POZ Protein, NAC-1 is related to Tumor Recurrence and is essential for Tumor Growth and Survival;" Proc. Natl. Acad. Sci. U.S.A., 2006; pp. 18739-18744.
J.M. Shih; "Application of Human Leukocyte Antigen-G Expression in the Diagnosis of Human Cancer;" Hum. Immunol., 2007; pp. 272-276.
I.M. Shih, M. Nesbit, M. Herlyn, et al.; "A New Mel-CAM (CD146)-Specific Monoclonal Antibody, MN-4, on Paraffin-Embedded Tissue;" Mod. Pathol., 1998; pp. 1098-1106.
I.M. Shih, R.J. Kurman; "The Pathology of Intermediate Trophoblastic Tumors and Tumor-Like Lesions;" Int. J. Gynecol. Pathol., 2001; pp. 31-47.
J. Simard, M.L. Ricketts, S. Gingras, et al.; "Molecular Biology of the 3Beta-Hydroxysteroid Dehydrogenase/Delta5-Delta1 Isomerase Gene Family;" Endocr. Rev., 2005; pp. 525-582.
G. Singer, R.J. Kurman, M. McMaster, et al.; "HLA-G Immunoreactivity is Specific for Intermediate Trophoblast in Gestational Trophoblastic Disease and Can Serve as a Useful Marker in Differential Diagnosis;" Am. J. Surg. Pathol., 2002; pp. 914-920.
G. Singer, V. Rebmann, Y-C Chen, et al.; "HLA-G is a Potential Tumor Marker in Malignant Ascites;" Clin, Cancer Res., 2003; pp. 4460-4464.
M.J. Yen, C.Y. Hsu, T.L. Mao, et al.; "Diffuse Mesothelin Expression Correlates with Prolonged Patient Survival in Ovarian Serous Carcinoma;" Clin. Cancer Res., 2006; pp. 827-831.

* cited by examiner

*Primary Examiner*—Lisa V Cook
(74) *Attorney, Agent, or Firm*—Thomas, Kayden, Horstemeyer & Risley

(57) ABSTRACT

A relatively specific trophoblastic-associated biomarker, HSD3B1, is disclosed. A method for screening gestational trophoblastic disease using HSD3B1 is also disclosed.

7 Claims, 5 Drawing Sheets
(3 of 5 Drawing Sheet(s) Filed in Color)

BIOMARKER FOR GESTATIONAL TROPHOBLASTIC DISEASE

CROSS-REFERENCE TO RELATED APPLICATION

This application claims the priority benefit of provisional application Ser. No. 60/841,667, filed Aug. 31, 2006, the full disclosure of which is incorporated herein by reference.

BACKGROUND

1. Field of Invention

The present invention relates to cancer biology. More particularly, the present invention relates to a biomarker for gestational trophoblastic disease.

2. Description of Related Art

Gestational trophoblastic disease can be broadly divided into three groups: hydatidiform moles which represent abnormal placentas, tumor-like lesions and trophoblastic neoplasms. In recent years, progress has been made in elucidating the biology of human trophoblast, especially in identifying trophoblast-associated biomarkers. Characterization of these biomarkers has led to a further understanding of the lineage and differentiation program of trophoblast and various forms of trophoblastic tumors and tumor-like lesions. It is now clear that trophoblastic tumors and tumor-like lesions recapitulate the trophoblast present in the early developing placenta and implantation site.

Differentiation of trophoblastic tumors and tumor-like lesions from non-trophoblastic neoplasms can be difficult based on morphology alone. Although several trophoblastic biomarkers have been previously identified such as hPL, hCG, Mel-CAM (CD146), HLA-G, cytokeratin 18 and inhibin-α, there are several problems associated with their use.

First, most of the previously known trophoblast-associated biomarkers are not specific to trophoblastic lineage. For example, Mel-CAM and HLA-G can be expressed in certain normal adult tissues and several malignant neoplasms [Shih I M, Nesbit M, Herlyn M et al. A new Mel-CAM (CD146)-specific monoclonal antibody, MN-4, on paraffin-embedded tissue. Mod Pathol. 1998, 11:1098-106; Shih Ie M. Application of human leukocyte antigen-g expression in the diagnosis of human cancer. Hum Immunol. 2007, 68:272-6].

Second, most of the trophoblastic biomarkers reported so far are only expressed in certain subtypes of trophoblastic cells. For example, hPL and Mel-CAM are predominantly expressed in implantation site intermediate trophoblast and only very focally in chorionic-type intermediate trophoblastic cells. Thus, hPL and Mel-CAM serve as biomarkers for placental site trophoblastic tumor (PSTT) but not for epithelioid trophoblastic tumor (ETT) and placental site nodules (PSN) which are related to chorionic-type intermediate trophoblastic cells. Similarly, p63 immunoreactivity can only be detected in chorionic-type intermediate trophoblastic cells and the related lesions including ETT and PSN but not in PSTT.

Third, antibodies that react specifically to some of the trophoblast-associated biomarkers on paraffin sections are not currently available from commercial sources. For example, commercially available antibodies to HLA-G and anti-Mel-CAM not as specific and sensitive when used on paraffin sections as compared to 4H84 monoclonal antibody [McMaster M T, Librach C L, Zhou Y et al. Human placental HLA-G expression is restricted to differentiated cytotrophoblasts. J. Immunol. 1995, 154:3771-8.; Singer G, Kurman R J, McMaster M et al. HLA-G immunoreactivity is specific for intermediate trophoblast in gestational trophoblastic disease and can serve as a useful marker in differential diagnosis. Am J Surg Pathol. 2002, 26 (7):914-20] and MN-4 monoclonal antibody [Shih I M, Nesbit M, Herlyn M et al. A new Mel-CAM (CD146)-specific monoclonal antibody, MN-4, on paraffin-embedded tissue. Mod Pathol. 1998, 11:1098-106] that recognize HLA-G and Mel-CAM epitope, respectively. Both 4H84 and MN-4 antibodies have been well characterized and extensively used for research purposes but they are not yet commercially available.

SUMMARY

A relatively specific trophoblastic-associated biomarker, HSD3B1, is disclosed. A method for screening gestational trophoblastic disease uses HSD3B1 is also disclosed.

BRIEF DESCRIPTION OF THE DRAWINGS

The file of this patent contains at least one drawing executed in color. Copies of this patent with the color drawing(s) will be provided by the Patent and Trademark Office upon request and payment of the necessary fee.

The invention can be more fully understood by reading the following detailed description of the embodiment, with reference made to the accompanying drawings as follows.

DETAILED DESCRIPTION

Figure 1:
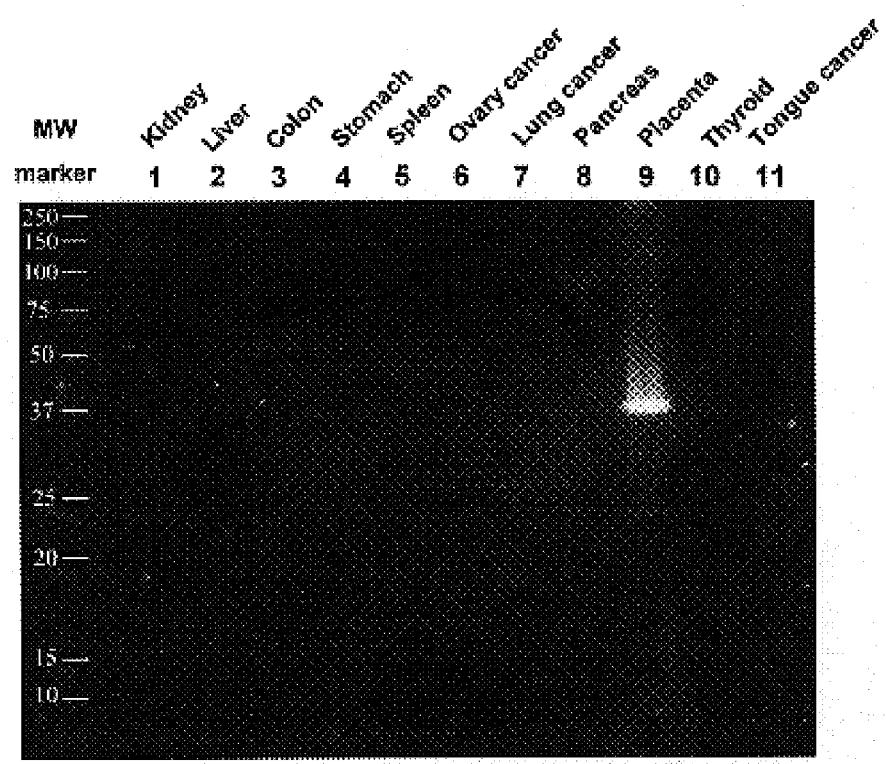
FIG. 1 shows Western blot analysis of HSD3B1 proteins in tissue lysates.

Abbreviation List
  CC: choriocarcinoma;
  EPS: exaggerated placental site;
  ETT: epitheloid trophoblastic tumor;
  NGTN: non-trophoblastic neoplasms;
  PSN: placental site nodule; and
  PSTT: placental site trophoblastic tumor.

Biomarker for Gestational Trophoblastic Disease: HSD3B1

A novel trophoblast-associated biomarker, HSD3B1, is disclosed. The full name of HSD3B1 is hydroxyl-α-5-steroid dehydrogenase, also known as 3β- and steroid δ-isomerase 1 (GeneBank Accession # BC031999). This enzyme catalyzes the oxidative conversion of delta 5-3 beta-hydroxy steroids to the delta 4-3-keto configuration and is involved in steroid hormone synthesis [Simard J, Ricketts M L, Gingras S et al. Molecular biology of the 3betahydroxysteroid dehydrogenase/delta5-delta4 isomerase gene family. Endocr Rev. 2005, 26:525-82].

Tissue Samples

Tissue samples used in this study included 19 PSNs, 18 ETTs, 9 EPS, 12 PSTTs, 35 CCs, 86 squamous cell carcinomas of the cervix, 16 adenocarcinomas of the cervix, 63 endometrial carcinomas of the uterus (59 endometrioid, 3 serous and one clear cell carcinomas), 84 lung carcinomas and 70 infiltrating ductal breast carcinomas. Except for small PSNs, all the lesions were arranged into tissue microarrays (TMAs). For the latter, three representative 1.5 mm cores or two 2 mm cores from each lesion were included. The 1.5 mm TMAs were constructed at the Johns Hopkins Tissue Microarray Facility and the 2 mm TMAs were constructed using a tissue microarray kit (UNITMA Inc., Korea). All the cases were anonymized and the use of archival tissues was approved by the institutional review board.

Western Blot Analysis

Western blot analysis was performed on 11 representative normal and tumor tissues, including the protein lysate obtained from kidney, liver, colon, stomach, spleen, thyroid, pancreas, placenta and carcinomas from ovary, lung and tongue. Similar amounts of total protein from each lysate were loaded and separated on 12% Tris-Glycine-SDS polyacrylamide gels (Novex, San Diego, Calif.), then electroblotted to the Millipore Immobilon-P polyvinylidene difluoride membranes as previously described [Singer G, Rebmann V, Y-C C et al. HLA-G is a potential tumor marker in malignant ascites. Clin Cancer Res. 2003, 9:4460-64.], which is incorporated here entirely by reference. The membranes were probed with the anti-HSD3B1 mouse monoclonal antibody, clone 3C11-D4, IgG1, at a concentration of 1 µg/ml (Abnova, Taipei, Taiwan) followed by a peroxidase conjugated goat anti-mouse immunoglobulin (1:2,500). Western blots were developed by chemiluminescence (Pierce, Rockford, Ill.).

FIG. 1 shows Western blot analysis of HSD3B1 proteins in tissue lysates. Equal amount of protein (25 µg) was loaded for each lane. Only placental tissue expresses HSD3B1 proteins as evidenced by a single band with a molecular weight of 42 kDa. Other tissues do not express HSD3B1. There was no detectable cross reactivity with other proteins as revealed in the Western blot analysis.

HSD3B1 SAGE Tag Analysis

To determine the HSD3B1 expression levels among normal tissues and tumor samples, the Serial Analysis of Gene Expression (SAGE) publicly accessible data base available on the web site of the Cancer Genome Anatomy Project (CGAP) [Boon K, Osorio E C, Greenhut S F et al. An anatomy of normal and malignant gene expression. *Proc Natl Acad Sci USA*. 2002, 99:11287-92; Lal A, Lash A E, Altschul S F et al. A public database for gene expression in human cancers. *Cancer Res*. 1999, 59:5403-7] was analyzed.

SAGE is a genome-wide technology that profiles global gene expression within a given tissue sample based on the counting of specific sequence tags that represent each gene in a transcriptome. SAGE libraries have been used successfully in identifying new biomarkers and assessing the expression pattern of a known gene among various tissues and tumors [Yen M J, Hsu C Y, Mao T L et al. Diffuse mesothelin expression correlates with prolonged patient survival in ovarian serous carcinoma. *Clin Cancer Res*. 2006, 12:827-31; Chen Y-C, Pohl G, Wang T-L et al. Apolipoprotein E is required for cell proliferation and survival in ovarian cancer. *Cancer Res*. 2005, 65:331-37; Nakayama K, Nakayama N, Davidson B et al. A BTB/POZ protein, NAC-1,is related to tumor recurrence and is essential for tumor growth and survival. *Proc Natl Acad Sci USA*. 2006].

In this study, this database was used to analyze the HSD3B1 expression in silica by comparing HSD3B1 tag counts among 159 human SAGE libraries as listed in Table 1.

The HSD3B1 specific tags were TGGTTTGCTGTTACCAA (SEQ ID NO: 1, for long SAGE) and TGGTTTGCTG (SEQ ID NO: 2, for conventional SAGE). HSD3B1 tag counts for each library were retrieved by filtering for tag sequences that matched uniquely to the HSD3B1 gene according to the Oct. 22, 2006 SAGE Map available on the web site of the National Center for Biotechnology Information (NCBI). Using a minimum tag count setting of >2, the HSD3B1 tags were tallied and normalized per 100,000 total tags for each SAGE library.

The counted result of the tag of HSD3B1 among 159 SAGE libraries showed none of the libraries contained the HSD3B1 tag, indicating undetectable expression levels of the HSD3B1 gene in non-placental libraries. Therefore, it is likely that HSD3B1 is a highly specific trophoblast-associated biomarker.

TABLE 1

A list of human SAGE libraries, from either tissue samples or cell clones, used to analyze HSD3B1 expression in silica.

| Tissue | Types | Library number |
|---|---|---|
| Brain | GBM | 10* (4)** |
| | Astrocytoma | 11 (10) |
| | Medulloblastoma | 25 (21) |
| | Oligodendroglioma | 2 (2) |
| | Ependymoma | 9 (9) |
| | Normal brain tissue | 7 (7) |
| | Normal spinal cord tissue | 1 (1) |
| Breast | DCIS | 5 (5) |
| | ICD | 13 (6) |
| | Normal breast | 7 (6) |
| Stomach | Adenocarcinoma | 9 (9) |
| | Normal stomach | 1 (1) |
| Colorectum | Adenocarcinoma | 3 (0) |
| | Normal colon | 3 (2) |
| Pancreas | Adenocarcinoma | 4 (0) |
| | Normal pancreas | 3 (1) |
| Prostate | Adenocarcinoma | 11 (4) |
| | Normal prostate | 1 (1) |
| Skin | Kaposi's sarcoma | 2 (2) |
| | Actinic kratosis | 2 (2) |
| Ovary | Adenocarcinoma | 9 (4) |
| | Normal ovary | 2 (0) |
| Mesothelium | Mesothelioma | 2 (2) |
| | Normal mesothelium | 1 (0) |
| Endothelium | Hemangioma | 1 (1) |
| | Endothelial cells | 2 (0) |
| Heart | | 2 |
| Lung | | 1 |
| Liver | | 1 |
| Skeletal muscle | | 2 |
| Kidney | | 1 |
| Eye | | 6 |

*Total library number.
**Library number from tissue samples.

Immunohistochemistry 21 early placentas and 18 complete hydatidiform moles were analyzed in this immunohistochemistry study. The anti-HSD3B1 antibody used in this study was a purified mouse monoclonal antibody (clone 3C11-D4, IgG1; provided by Abnova Corporation, Taipei, Taiwan,) raised against a full-length recombinant HSD3B11. This clone of antibody, 3C11-D4, recognizes HSD3B1 specifically, and does not cross react with other proteins while cross-reactivity had been frequently shown in many antibodies. Antigen retrieval was performed by boiling the sections in citrate buffer (pH 6.0) in a 95° C. water bath for 20 min. After incubation with the primary antibody at 4° C. overnight, a positive reaction in tissue sections was detected by the EnVision+System (DAKO, Carpinteria, Calif.) and was developed with 3,3'-diaminobenzidine. Scoring of HSD3B11 immunoreactivity was based on a combination of the percentage of positively stained cells and the intensity of the nuclear staining ranging from 0 to 4+ using the H score [Budwit-Novotny D A, McCarty K S, Cox E B et al. Immunohistochemical analyses of estrogen receptor in endometrial adenocarcinoma using a monoclonal antibody. *Cancer Res.* 1986, 46:5419-25], which is incorporated here entirely by reference. The H-score was calculated using the following equation: H-score=ΣPi(i+1), where i is the intensity of the stained tumor cells (0 to 4+), and Pi is the percentage of stained tumor cells for each intensity varying from 0 to 100%. This semi-quantitative analysis has been shown to have high intra-observer and inter-observer reproducibility [Lessey B A, Castelbaum A J, Wolf L et al. Use of integrins to date the endometrium. *Fertil Steril.* 2000, 73:779-87], which is incorporated here entirely by reference.

Figure 2:
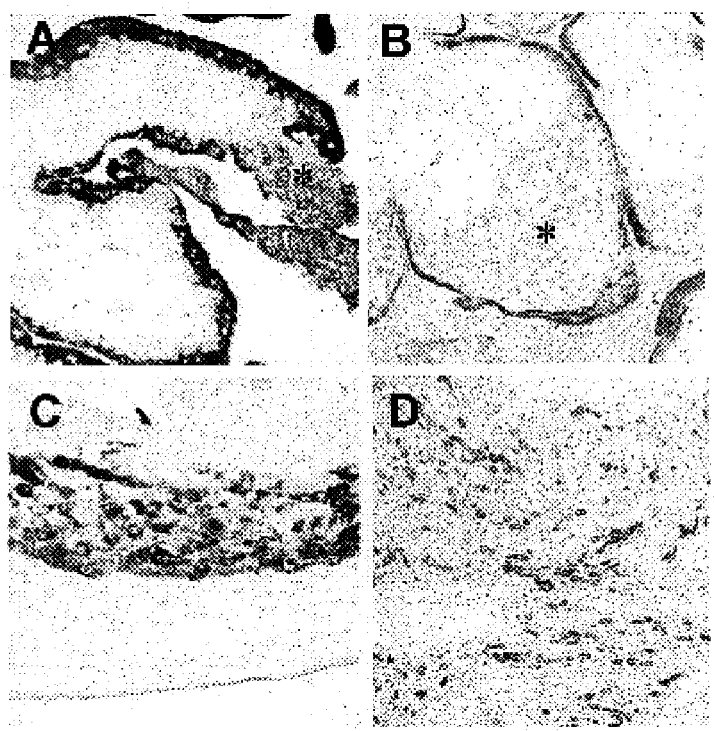
FIGS. 2A-2D are representative photomicrographs showing HSD3B1 staining patterns in normal early placentas.

FIGS. 2A-2D are representative photomicrographs showing HSD3B1 staining patterns in normal early placentas. HSD3B1 immunoreactivity was present in syncytiotrophoblast and was variable in intermediate trophoblastic cells (marked by asterisk) in trophoblastic columns (FIGS. 2A and 2B). Cytotrophoblastic cells were negative for the staining. HSD3B1 staining was detectable in the intermediate trophoblastic cells in chorion leaves (FIG. 2C) and implantation site (FIG. 2D). The result showed that HSD3B1 was highly expressed in syncytiotrophoblast, intermediate trophoblastic cells in the implantation site and the chorion leaves in normal placentas. The expression of HSD3B1 in intermediate trophoblastic cells in the trophoblastic column was highly variable with 11% of placentas being positive. In contrast, HSD3B1 staining was undetectable in cytotrophoblastic cells.

Figure 3:
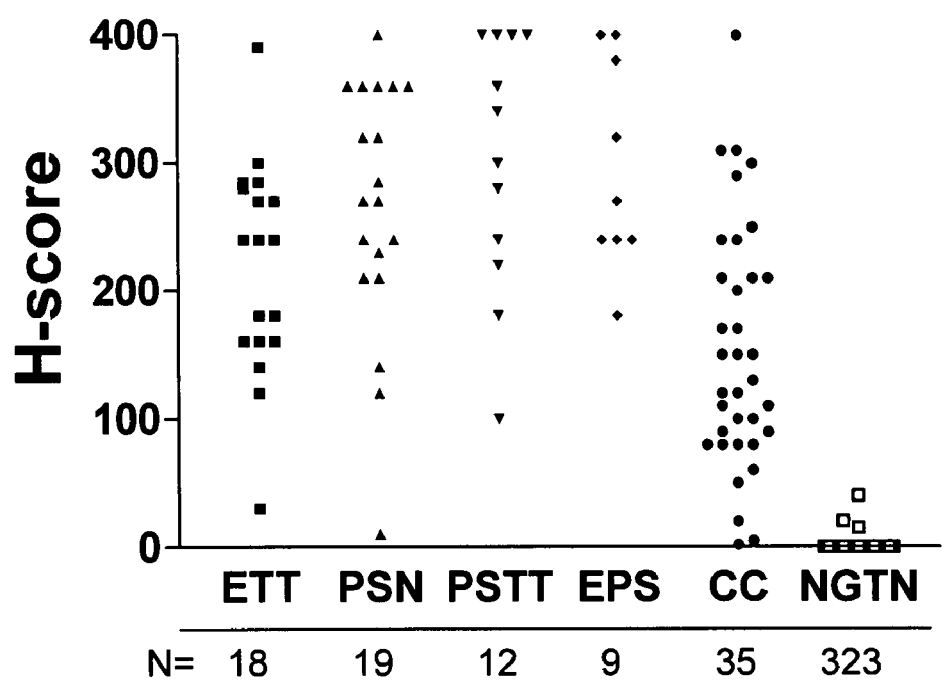
FIG. 3 is a scatter plot of H scores of HSD3B1 immunostaining in different trophoblastic tumors and tumor-like lesions as well as non-trophoblastic carcinomas from uterus, lung and breast.

FIG. 3 is a scatter plot of H scores of HSD3B1 immunostaining in different trophoblastic tumors and tumor-like lesions as well as non-trophoblastic carcinomas from uterus, lung and breast. From FIG. 3, immunohistochemistry using this anti-HSD3B1 antibody on trophoblastic tumors and tumor-like lesions as well as on a variety of uterine and lung carcinomas in paraffin sections showed the following: all normal placentas (n=21), choriocarcinoma (CC; n=35), placental site trophoblastic tumor (PSTT; n=12), epitheloid trophoblastic tumor (ETT; n=18), placental site nodule (PSN; n=19) and exaggerated placental site (EPS; n=9) expressed HSD3B1 in almost all of the trophoblastic cells.

Among trophoblastic tumors and tumor-like lesions, several choriocarcinomas had low H-scores. Normal endometrial glands, myometrium and cervix were negative for HSD3B1 expression. In contrast, HSD3B1 immunoreactivity was not detected in a wide variety of uterine, lung and breast carcinomas except three specimens (two endometrioid carcinoma and one breast carcinoma), which showed focal and weak staining. The H-score of trophoblastic tumors and tumor-like lesions was significantly higher than that of non-trophoblastic carcinoma (p<0.0001, paired t-test).

Figure 4:
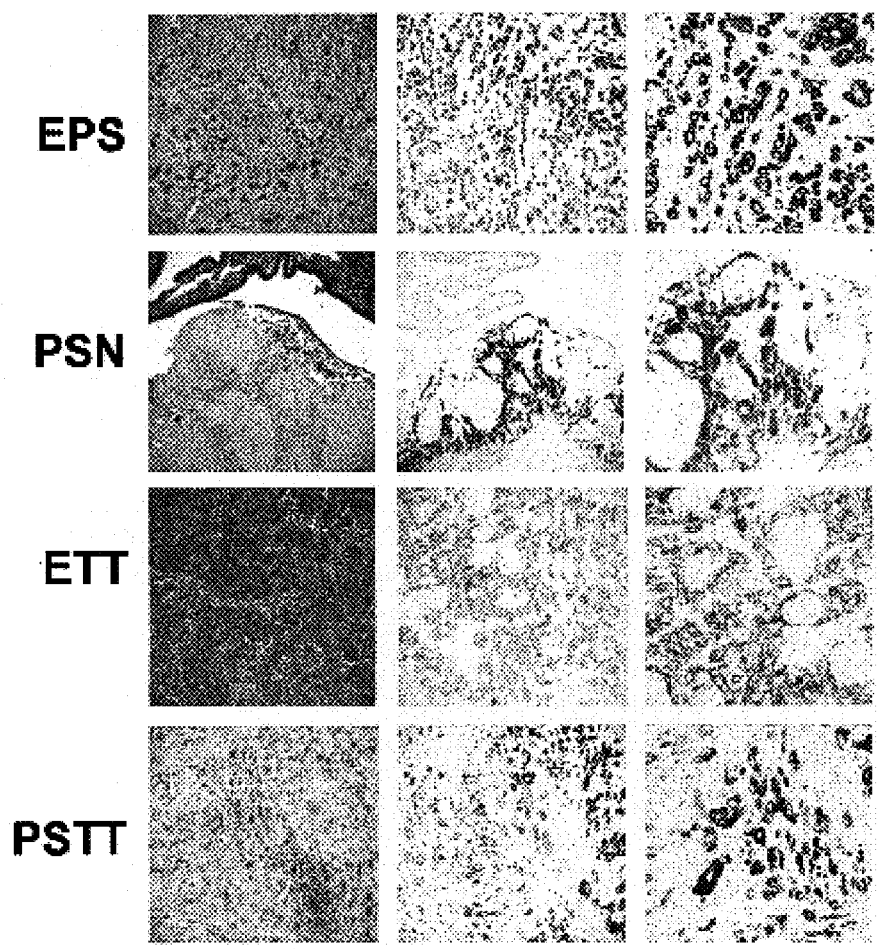
FIG. 4 shows representative photomicrographs showing HSD3B1 staining patterns in trophoblastic tumors and tumor-like lesions.

FIG. 4 shows representative photomicrographs showing HSD3B1 staining patterns in trophoblastic tumors and tumor-like lesions. The left column is hematoxylin and eosin staining, the middle and right columns are the HSD3B1 antibody stained sections under low magnification power (100×) and medium magnification power (400×), respectively.

FIGS. 5A-5F are representative photomicrographs showing HSD3B1 staining patterns in a choriocarcinoma and a representative non-trophoblastic carcinoma. Choriocarcinoma expresses high levels of HSD3B1 (FIGS. 5A-5C) but a squamous carcinoma of the lung (FIGS. 5D-5F) does not. FIGS. 5A and 5D are hematoxylin and eosin stained sections.

Figure 5:
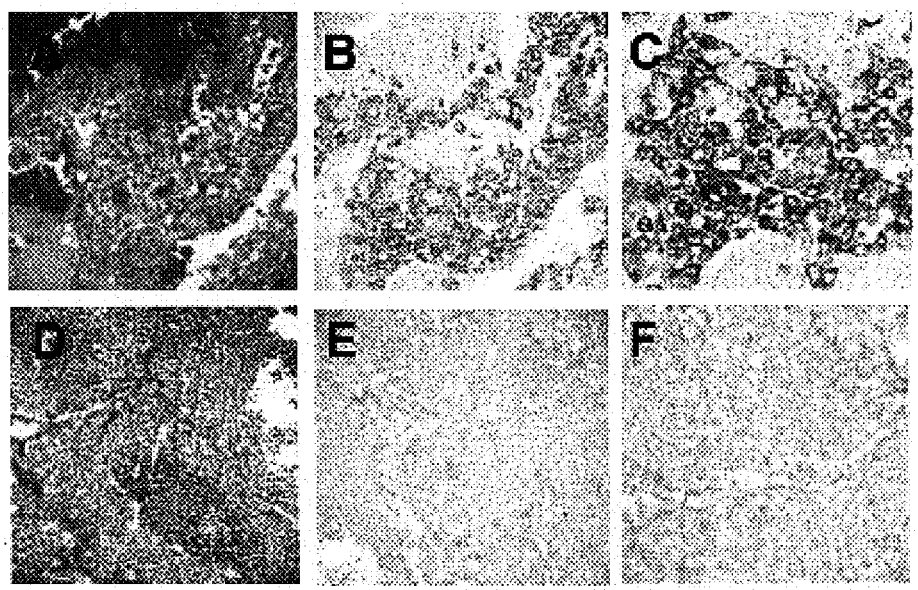
FIGS. 5A-5F are representative photomicrographs showing HSD3B1 staining patterns in a choriocarcinoma and a representative non-trophoblastic carcinoma.

From FIGS. 4-5, it was found that HSD3B1 immunoreactivity was localized in the cytoplasm of trophoblastic cells but not in the surrounding stromal cells and inflammatory cells.

Discussion

From the results showed above, the HSD3B1 expression is relatively restricted to trophoblastic lineage, i.e. trophoblastic tumors and tumor-like lesions of trophoblast, based on SAGE tag counts, western blot analysis and immunohistochemistry. HSD3B1 is essentially expressed in all syncytiotrophoblast and almost all implantation and chorionic type intermediate trophoblastic cells in the implantation site and chorionic leave. HSD3B1 has a similar pattern of expression in CCs, PSTTs, ETTs, PSNs and EPSs. In some CCs, the intermediate trophoblastic cells do not express HSD3B1. This observation suggests that these trophoblastic cells are related to the intermediate trophoblastic cells located in the trophoblastic column rather than the intermediate trophoblastic cells in the implantation sites.

These findings suggest that anti-HSD3B1 antibody may be used alone or in combination with other commercially available antibodies in cases that are suspicious for trophoblastic tumors and tumor-like lesions. The diffuse and intense immunostaining pattern of HSD-3B1 in the majority of trophoblastic tumors and tumor-like lesions distinguishes them from other non-trophoblastic carcinomas of the uterus and lung, which are rarely positive for HSD-3B1. Very few of the non-trophoblastic neoplasms examined were positive for HSD-3B1. In those that were positive, the immunointensity is weaker and the distribution more focal than trophoblastic tumors and tumor-like lesions.

It will be apparent to those skilled in the art that various modifications and variations can be made to the structure of the present invention without departing from the scope or spirit of the invention. For example, the monoclonal antibody capable of recognizing the HSD3B1 can be replaced by polyclonal antibody, phage display antibody, antibody fragment, recombinant antibody, such as chimeric antibody and CDR-grafted antibody, and any other usable candidate compounds while the candidate compounds can be obtained by using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation), and aptamer libraries.

In addition to immunohistochemical assay, any other kinds of usable assay, such as an immunological assay, that can detect the presence or level of HSD3B1 in a biological sample can also be used to diagnose the gestational trophoblastic disease. For examples, the immunological assay described above includes Western blot, enzyme-linked immunosorbent assay (ELISA), or radiation immune assay (RIA).

Since HSD3B1 is a highly specific trophoblast-associated biomarker, another usable assay is to detect the abundance of mRNA of HSD3B1 whereas the expression of HSD3B1 protein is from mRNA. The abundance of mRNA of HSD3B1 can be detected by, for example, fluorescence in situ hybridization (FISH) assay or quantitative RT-PCR reaction.

In view of the foregoing, it is intended that the present invention cover modifications and variations of this invention provided they fall within the scope of the following claims and their equivalents.

What is claimed is:

1. A method for screening gestational trophoblastic disease, comprising:
  detecting the presence or level of Hydroxy-δ-5-steroid dehydrogenase, 3β- and steroid δ-isomerase 1 (HSD3B1) in a biological sample of a subject and correlating said detection to gestational trophoblastic disease.

2. The method of claim 1, wherein the presence or level of the HSD3B1 is determined by contacting the biological sample with an antibody that specifically binds to the HSD3B1 and assessing the binding between the HSD3B1 and the antibody.

3. The method of claim 2, wherein the antibody is a monoclonal antibody, a polyclonal antibody, an antibody fragment, a recombinant antibody, or a phage display antibody.

4. The method of claim 3, wherein the recombinant antibody is a chimeric antibody or a CDR-grafted antibody.

5. The method of claim 1, wherein the presence or level of the HSD3B1 is determined by contacting the biological sample with a chemical compound that specifically binds to the HSD3B1 and assessing the binding between the HSD3B1 and the chemical compound.

6. The method of claim 5, wherein the chemical compound is selected from combinatorial libraries.

7. The method of claim 1, wherein the biological sample is from a tissue of the trophoblastic cell type.

* * * * *

SEQUENCE LISTING

<160> NUMBER OF SEQ ID NOS: 2

<210> SEQ ID NO 1
<211> LENGTH: 17
<212> TYPE: DNA
<213> ORGANISM: Homo sapiens

<400> SEQUENCE: 1
tggtttgctg ttaccaa                                                17

<210> SEQ ID NO 2
<211> LENGTH: 10
<212> TYPE: DNA
<213> ORGANISM: Homo sapiens

<400> SEQUENCE: 2
tggtttgctg                                                        10